United States Patent [19]
Savage et al.

[11] Patent Number: 5,979,453
[45] Date of Patent: Nov. 9, 1999

[54] NEEDLE MYOLYSIS SYSTEM FOR UTERINE FIBRIODS

[75] Inventors: George M. Savage, Portola Valley; Margaret Webber, Los Altos, both of Calif.

[73] Assignee: FemRx, Inc., Sunnyvale, Calif.

[21] Appl. No.: 08/744,610

[22] Filed: Nov. 6, 1996

Related U.S. Application Data

[60] Provisional application No. 60/006,396, Nov. 9, 1995.
[51] Int. Cl.$^6$ .................................................. A61B 17/39
[52] U.S. Cl. ......................... 128/898; 606/41; 600/454; 600/461
[58] Field of Search ........................ 606/41, 42, 45–50; 604/21, 22; 607/100–102; 600/453, 454, 461, 462

[56] References Cited

U.S. PATENT DOCUMENTS

| | | |
|---|---|---|
| 3,556,079 | 1/1971 | Omizo . |
| 3,698,394 | 10/1972 | Piper et al. . |
| 4,887,606 | 12/1989 | Yock et al. . |
| 4,960,109 | 10/1990 | Lele . |
| 5,192,267 | 3/1993 | Shapira et al. . |
| 5,209,721 | 5/1993 | Wilk . |
| 5,259,385 | 11/1993 | Miller et al. . |
| 5,259,386 | 11/1993 | Sharkawy . |
| 5,323,778 | 6/1994 | Kandarpa et al. . |
| 5,335,663 | 8/1994 | Oakley et al. . |
| 5,336,111 | 8/1994 | Durgin, Jr. et al. ....................... 606/50 |
| 5,342,298 | 8/1994 | Michaels et al. . |
| 5,368,032 | 11/1994 | Cline et al. . |
| 5,370,675 | 12/1994 | Edwards et al. ......................... 607/101 |
| 5,383,876 | 1/1995 | Nardella ................................... 606/49 |
| 5,385,544 | 1/1995 | Edwards et al. . |
| 5,391,144 | 2/1995 | Sakurai et al. . |
| 5,403,311 | 4/1995 | Abele et al. ............................... 606/49 |
| 5,447,510 | 9/1995 | Jensen . |
| 5,456,689 | 10/1995 | Kresch et al. . |
| 5,462,545 | 10/1995 | Wang et al. .............................. 606/41 |
| 5,472,441 | 12/1995 | Edwards et al. .......................... 606/41 |
| 5,536,267 | 7/1996 | Edwards et al. .......................... 606/41 |
| 5,556,396 | 9/1996 | Cohen et al. . |
| 5,588,432 | 12/1996 | Crowley .................................. 600/461 |
| 5,599,345 | 2/1997 | Edwards et al. .......................... 606/41 |
| 5,814,043 | 9/1998 | Shapeton ................................. 606/48 |

OTHER PUBLICATIONS

Baggish, Michael S. "The Nd:YAG Laser for Gynecologic Surgery," a publication by LaserSonics, Heraeus Surgical, Inc., Milpitas, California (1993).

Goldfarb, Herbert A. "Bipolar Laparoscopic Needles for Myoma Coagulation," *The Journal of the American Association of Gynecologic Laparoscopists*, 2(2):175–179 (Feb., 1995).

Goldfarb, Herbert A. "Comparison of Bipolar Electrocoagulation and Nd:YAG Laser Coagulation for Symptomatic Reduction of Uterine Myomas," *The Journal of the American Association of Gynecologic Laparoscopists*, (Aug., 1994).

Goldfarb, Herbert A. "Laparoscopic Coagulation of Myoma (Myolysis)," *Obstetrics and Gynecology Clinics of North America*, 22(4):807–819 (Dec., 1995).

(List continued on next page.)

*Primary Examiner*—Michael Peffley
*Attorney, Agent, or Firm*—Verne E. Kreger, Jr.

[57] ABSTRACT

The present invention provides electrosurgical needles, needle systems, and methods for their use which will allow the surgeon to target a tumor's blood supply. Generally, the invention facilities targeting the bloodflow of the tumor by incorporating a doppler ultrasound transducer into the needle or needle sheath. Preferably, the surgeon will also be able to control the temperature of the needle using an integral temperature sensor to effect maximum transfer of the RF energy into the tissue, thereby maximizing the volume of tissue destroyed. Furthermore, when used (for example) in the treatment of uterine fibroids, the present invention will reduce damage to the serosa by monitoring the uterine surface temperature during myolysis through a temperature sensor integrated into the sheath holding the myolysis needle.

5 Claims, 2 Drawing Sheets

OTHER PUBLICATIONS

Goldfarb, Herbert A. "Nd:YAG Laser Laparoscopic Coagulation of Symptomatic Myomas," *The Journal of Reproductive Medicine*, 37(7):636–638 (Jul., 1992).

Goldfarb, Herbert A. "Selected Scientific Abstracts," *The Journal of the American Association of Gynecologic Laparoscopists*, 2(4):Supplement (Aug., 1995).

Goldfarb, Herbert A. "Removing Uterine Fibroids Laparoscopically," *Contemporary OB/GYN*, 39(2):1–9 (Feb., 1994).

Phillips, Douglas R. "Laparoscopic Myoma Coagulation (Myolysis)," *New Developments in Medicine & Drug Therapy*, 3(3):1 (May/Jun. 1994).

Phillips, Douglas R. "Laparoscopic Leiomyoma Coagulation (Myolysis)," *Gynecological Endoscopy* 4:5–11 (1995).

Wood, Carl "Alternative Treatment," *Bailliere's Clinical Obstetrics and Gynecology*, 9(2):373–397 (Jun., 1995).

NEEDLE MYOLYSIS SYSTEM FOR UTERINE FIBRIODS

CROSS-REFERENCE DATA

This application is a continuation-in-part of U.S. Provisional Application Ser. No. 60/006,396, filed Nov. 9, 1995, the full disclosure of which is incorporated herein by reference.

BACKGROUND OF THE INVENTION

Benign leiomyomata (uterine fibroids) are common tumors which affect more than 25% of all women at some time during the reproductive years. Many women wish to have fibroid-related symptoms such as bleeding and pain treated without resort to hysterectomy. Pharmacologic therapy alone is of limited utility due to side-effects associated with long-term use. Hysteroscopic resection using the loop or vaporizing resectoscope is appropriate for those tumors which protrude into the uterine cavity—so called submucous myomas. Surgical myomectormy (removal of the fibroid) is often used for tumors which are thought to be the cause of infertility. However, this approach usually requires a laparotomy and is often associated with adhesion formation between the uterus, bowel and other adjacent structures. These adhesions can be the cause of chronic pain in some patients.

Needle myolysis is a promising technique whereby a laparoscope is used to introduce one or more needles into a fibroid tumor under visual control. Bipolar Radio Frequency ("RF") current is then delivered between two adjacent needles, or unipolar current between a single needle and a distant dispersive electrode affixed to the thigh or back. The aim of needle myolysis is to coagulate a significant volume of the tumor and thereby cause it to shrink substantially. The traditional technique is to make multiple passes through different areas of the tumor using the coagulating needle to destroy many cylindrical cores of abnormal tissue. However, the desirability of multiple passes is mitigated by the risk of adhesion formation, which is thought to increase with increasing amounts of injured uterine serosa, and by the operative time and skill required.

Recently, Goldrath and others have demonstrated that tumor shrinkage can be preferentially induced by destroying the tumor's blood supply, which is generally located on the periphery, rather than by targeting the bulk of the fibroid. Physicians acting on this observation use the needles to ring the tumor with cores of coagulation. This technique still calls for multiple tumor passes and, in the end, the operator remains uncertain as to the status of the tumor's blood supply.

Another problem with needle myolysis is the variability in generated lesion sizes created by the electrocautery generator. Electrosurgical lesions are created when radiofrequency current flows through tissue, resistively heating it to the point of cell death. It has been demonstrated in the RF catheter ablation literature and elsewhere that maximum energy transfer occurs when the electrode tissue interface temperature remains below 100° C. Temperatures in excess of 100° C. cause intracellular water to boil, desiccating tissue and reducing the electrical and thermal conductivity of the surrounding tissue. Under such conditions, the impedance seen by the ESU increases and current flow falls (since most ESUs are constant voltage sources). Since the electrocautery electrode itself acts as a passive heat sink, the highest tissue temperature is usually found at some depth from the tissue-electrode interface. Therefore, under ideal circumstances the coagulating electrode temperature would be maintained at some level below the critical 100° C. temperature (e.g., 80° C.).

Today, the surgeon must set ESU power levels based upon heuristics. However, the amount of energy required to maintain the tissue-electrode interface at the desired temperature will vary depending upon a number of factors, including the size of the coagulating needle, the blood flow in the surrounding tissue, etc. Excessive temperatures at the uterine serosa can be expected to increase the incidence of adhesion formation; this can lead to chronic pain in some patients.

To overcome the above limitations, it would be desirable to provide improved needle myolysis systems and methods to facilitate the accurate, controlled targeting of a tumor's blood supply. It would further be desirable if such an apparatus could provide feedback regarding the temperature at the tissue-electrode interface, and particularly the temperature of nearby tissues.

SUMMARY OF THE INVENTION

The present invention provides electrosurgical needles, needle systems, and methods for their use which will allow the surgeon to target a tumor's blood supply. Generally, the invention facilities targeting the bloodflow of the tumor by incorporating a Doppler ultrasound transducer into the needle or needle sheath. Preferably, the surgeon will also be able to control the temperature of the needle using an integral temperature sensor to effect maximum transfer of the electrosurgical energy into the tissue, thereby maximizing the volume of tissue destroyed. Furthermore, when used (for example) in the treatment of uterine fibroids, the present invention will reduce damage to the serosa by monitoring the uterine surface temperature during myolysis through a temperature sensor integrated into the sheath surrounding the myolysis needle.

In a first aspect, the present invention provides an electrosurgical device comprising a needle having a proximal end and a distal end, with an ultrasound transducer near the distal end. A conductive surface is disposed near the distal end of the needle to induce heating of adjacent tissues when an electrical potential is applied. The transducer will preferably be coupled to a Doppler ultrasound system capable of sensing bloodflow. Advantageously, the transducer can thus be used to direct the insertion of the needle to specifically target and coagulate the bloodflow to a tumor.

In another aspect, the present invention provides an electrosurgical probe comprising a needle having a proximal end and a distal end. The distal end is adapted for insertion into a target tissue of a patient body. A conductive surface is disposed near the distal end of the needle, and is capable of heating the target tissue when the needle is inserted and an electrical potential is applied. An ultrasound transducer is mounted along the needle for directing insertion of the needle toward the target tissue.

The conductive surface and the transducer will typically be electrically and/or thermally isolated from each other. In some embodiments, the ultrasound transducer will be affixed to the needle itself and will be inserted toward the target tissue with that structure. In alternative embodiments, the transducer will be mounted on a sheath surrounding the needle, ideally being distally oriented to track the path of the needle when the transducer is placed against tissue and the needle is advanced distally from the sheath. Regardless, the transducer will generally comprise a phased-array capable of use with a Doppler ultrasound system for sensing and color imaging of bloodflows. A temperature sensor on the sheath will preferably provide feedback to the electrosurgical power source to further minimize damage to surrounding tissues.

In another aspect, the present invention provides an electrosurgical probe comprising a needle having a proximal end and a distal end, the distal end being adapted for insertion into a target tissue of a patient body. The needle has a conductive surface disposed near the distal end which is capable of heating the target tissue when the needle is inserted and an electrical potential is applied. A sheath is slidably disposed over the needle. A temperature sensor mounted on the needle or the sheath indicates the temperature of tissues adjacent the target tissue. Preferably, an ultrasound transducer is mounted on the needle or the sheath. The transducer is coupleable to a Doppler ultrasound system for directing insertion of the needle toward a bloodflow of the target tissue.

In another aspect, the present invention provides an electrosurgical system comprising a needle having a proximal end and a distal end, the distal end being adapted for insertion into a target tissue of a patient body. The needle has a conductive surface disposed near the distal end. An electrosurgical power source is coupled to the conductive surface for heating the target tissue. An ultrasound transducer is mounted along the needle, and a Doppler ultrasound system is coupled to the ultrasound transducer for directing insertion of the needle toward a bloodflow of the target tissue.

In another aspect, the present invention provides a method comprising inserting a needle of a probe into tissue adjacent a tumor. A bloodflow of the tissue is sensed with an ultrasound transducer of the probe. A conducive surface on the needle is energized with electrosurgical power to coagulate the bloodflow.

DETAILED DESCRIPTION OF THE SPECIFIC EMBODIMENTS

It should be noted that while the apparatus and methods of the present invention are particularly well suited for laparoscopically or hysteroscopically inducing shrinkage of fibroid tumors, the present invention will also have application in the treatment of other tumors, particularly the prostatic adenoma responsible for benign prostatic hyperplasia. Therefore, descriptions of utility in laparoscopic treatment of fibroid tumors should not be viewed as limiting the application of the technology. For example, application of a Doppler ultrasound coagulation needle to BPH through an operating cystoscope would also be possible.

Figure 1:
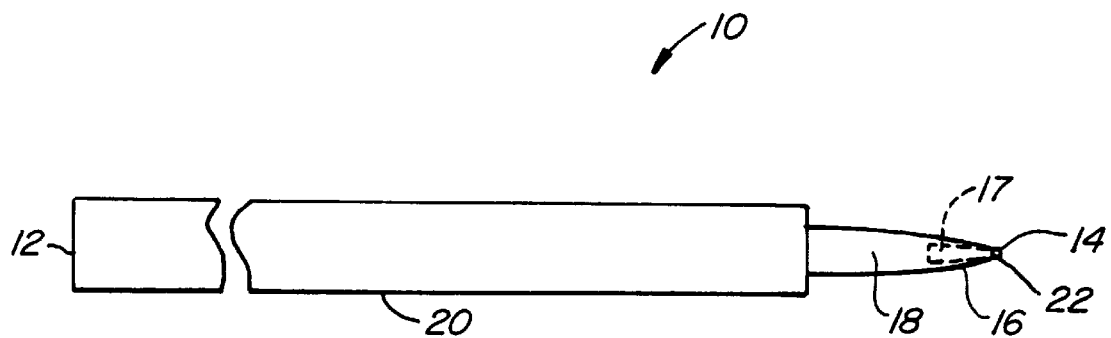
FIG. 1 is a schematic illustration of a myolysis needle according to the principles of the present invention.

Referring now to FIG. 1, a myolysis needle probe 10 generally includes a proximal end 12 and a distal end 14. A needle 16 includes an ultrasound transducer 17 near its distal end. The transducer has Doppler flow sensing capabilities when coupled to an appropriate ultrasound system. The needle further includes an external conductive surface 18 which is coupled to an electrosurgical power unit (ESU) through proximal end 12, and is generally retractable into a sheath 20. Hence, in this embodiment, the transducer will be inserted toward the target tissues with the needle.

Doppler ultrasound is used in medicine to detect blood flow. Doppler ultrasound technology has been integrated into stethoscopes, scanning ultrasound probes, and more recently, vascular access needles. An exemplary Doppler vascular access needle has been developed by Advanced Cardiovascular Systems, Inc., under the tradename Smart-Needle. A Doppler ultrasound guided needle is described in U.S. Pat. No. 5,259,385, the full disclosure of which is incorporated herein by reference.

The myolysis needle will preferably be equipped with a temperature sensor 22, such as a thermocouple or thermistor. This will enable the physician to monitor temperatures during a burn and adjust the power setting accordingly. Another alternative is to use the temperature sensor to close a feedback loop to the ESU, permitting continuous automatic temperature control at the ablating site. In this embodiment, the operator would set the desired needle temperature and maximum allowable ESU power. The ESU would then decrease power from the setpoint as required to avoid overshooting the set-point temperature. In this example, the surgeon would still see a real-time readout of the actual needle temperature. An exemplary electrosurgical feedback loop is described in U.S. Pat. No. 5,556,396, the full disclosure of which is incorporated by reference.

Figure 2:
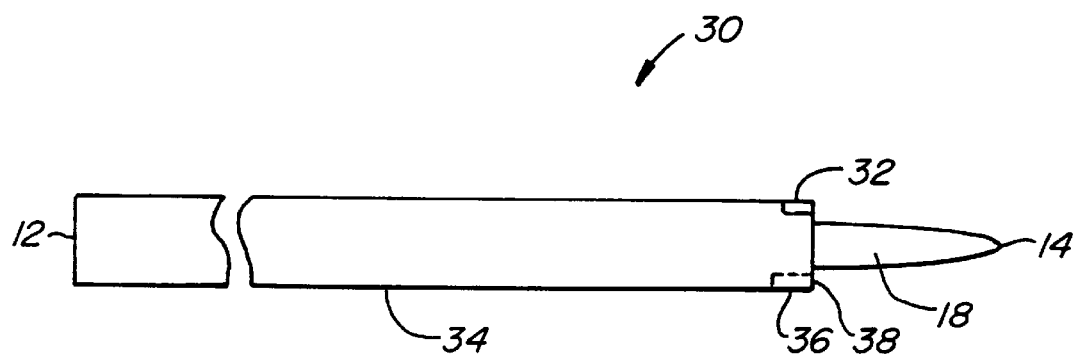
FIG. 2 is a schematic illustration of an alternative myolysis needle having a Doppler transducer mounted on the sheath, according to the principles of the present invention.

Needle probe 10 incorporates doppler ultrasound transducer 17 into the myolysis needle 16 itself. In an alternative needle probe 30, a sheath transducer 32 may be mounted on flow-sensing sheath 34, as shown in FIG. 2. The sheath transducer permits the surgeon to target the blood supply of a fibroid, prostatic adenoma, or other tumor by placing the end of the sheath against adjacent tissues. As is known in the art, the Doppler transducer will often provide an image of bloodflow along an image plane or surface. Preferably, sheath transducer 32 will be distally oriented so that the Doppler image can be used to direct distal advancement of the needle, the needle ideally being adjacent an image plane. Sheath transducer 32 will typically be offset to one side of the needle as shown, but may alternatively comprise an annular structure disposed coaxially about the needle, a plurality of transducers mounted about the needle, or the like.

In the preferred embodiment of the method of the present invention, the physician will locate the fibroid and extend the retractable needle to the appropriate depth and localize the blood supply with the sheath or needle mounted Doppler transducer. This information would be used to guide application of cautery with conductive surface 18. Note that if bipolar current is to be used, a pair of needles may be extended rather than a single needle. Regardless, this technique could reduce the number of passes required for definitive tumor reduction therapy, thereby reducing operating time and the risk of adhesion formation. Another benefit is that the surgeon would receive immediate feedback as to the elimination of the targeted blood flow from the Doppler ultrasound capabilities of the probe.

Referring still to FIG. 2, a sheath temperature sensor 36, typically a thermocouple or thermistor, can also be incorporated into the sheath surrounding the retractable myolysis needle. This sensor provides additional feedback on the coagulation process, and is particularly beneficial for minimizing damage to tissues surrounding those targeted for electrosurgical therapy. When pressed against the serosal surface of the uterus, for example, this thermal sensor can display the uterine surface temperature. An alarm can sound if the surface temperature exceeds a user-selected level (e.g., 45° C.). In the exemplary embodiment, the needle myolysis device is equipped with an irrigation port 38 so that the serosa is cooled by irrigation solution during the myolysis burn, still further minimizing trauma to surrounding tissues.

A wide variety of alternative electrosurgical needle structures and electrosurgical current pathways may be provided within the scope of the present invention. Generally, current delivery may be effected via a single needle in unipolar or monopolar mode, via a pair of needles in bipolar mode, or between a single needle and a distal surface of the sheath in an alternative bipolar arrangement. Alternatively, one or more myolysis needles could be energized by connecting electrically separated segments of each needle in parallel. In some embodiments, depending upon the amount of needle exposed from the sheath, a proximal needle segment between the conductive surface (or surfaces) and the sheath can be left inactive, thereby sparing the uterine serosa the direct effects of resistive heating. A simple device might have fixed or retractable needle(s) and an irrigation port for serosal cooling during current application. Optionally, where the needle electrode is fixed in position, and where surface cooling is provided via irrigation, only the distal portion of the needle will be active. This structure may optionally be used by slowly withdrawing the needle while applying electrosurgical energy. Other features, such as temperature sensing in the lesion, at the serosa, and Doppler assisted blood-flow localization could be added individually or together.

Each of these embodiments will preferably include a Doppler transducer integrated into the structure of the needle probe. The most likely route of introduction of this device would be through a laparoscope, although hysteroscopic and cystoscopic use is also possible.

Figure 3:
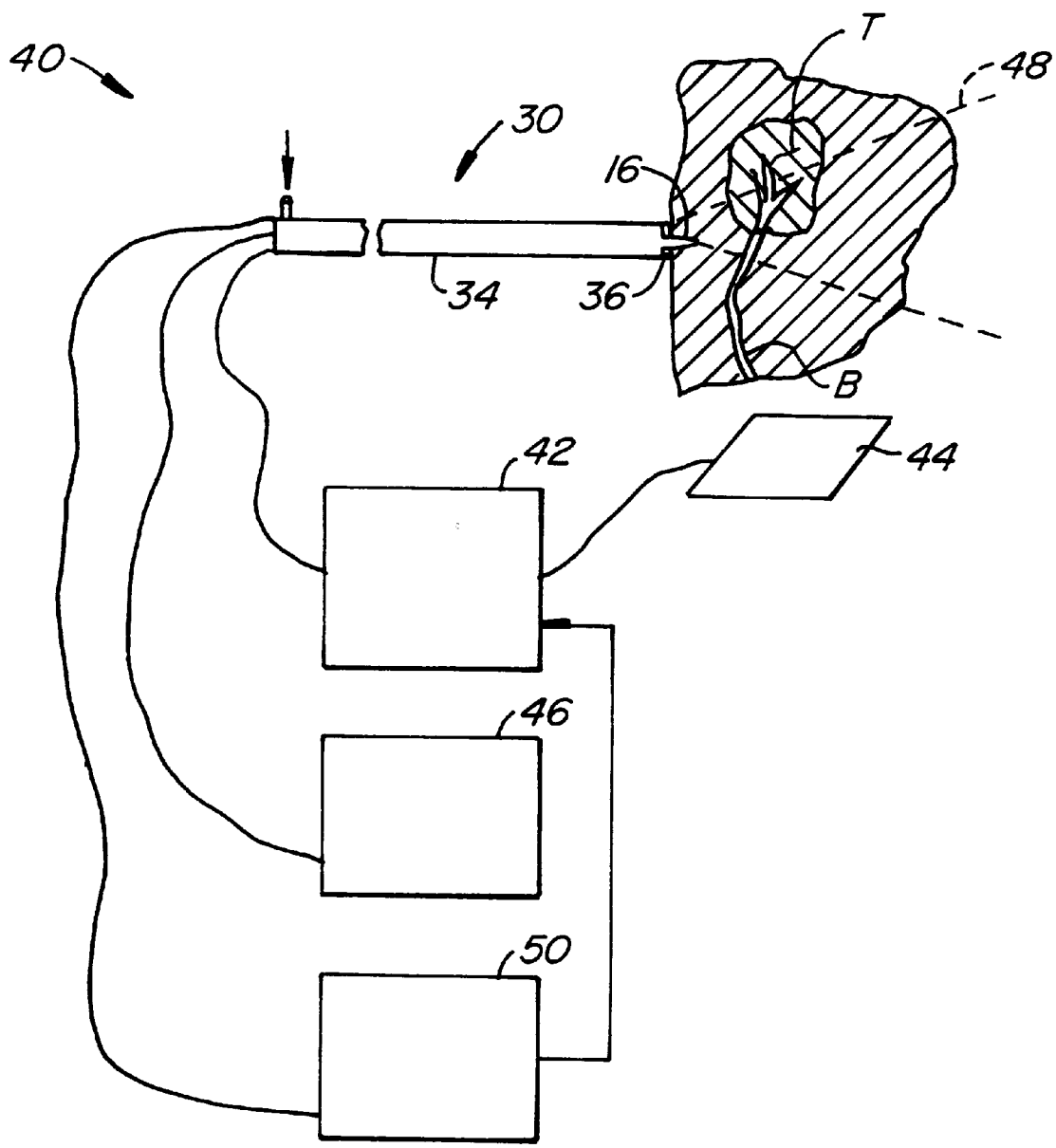
FIG. 3 schematically illustrates an electrosurgical system including the myolysis needle of FIG. 1, and also shows a method of using that system for the treatment of uterine fibroids.

An exemplary system and method for treating uterine fibroids is schematically illustrated in FIG. 3. In a needle system 40, needle probe 30 is coupled to an electrosurgical power unit 42. Here, the needle applies current in a monopolar mode, while dispersive electrode 44 will typically be affixed to the thigh or back, as described above. A Doppler ultrasound image system 46 is coupled to sheath transducer 32, providing an image of bloodflow at an image plane 48. As the needle and transducer are integrated into a single probe structure, and as needle 16 extends along image plane 48, the Doppler image greatly facilitates insertion of needle 16 distally from the sheath toward a bloodflow B of a tumor T. Once the Doppler image system indicates that the needle is adjacent the vessel which is supplying blood to the tumor, electrosurgical power is applied by ESU 42 through the needle to coagulate the bloodflow. Optionally, the temperature of the adjacent tissue is monitored during the burn by sheath temperature sensor 36. Ideally, the temperature sensor is coupled to the ESU through a temperature control system 50, so as to provide the necessary coagulation with minimal trauma, such as injury to the uterine serosa, adhesion formation, and the like. Cooling will typically be provided with a distal irrigation port of the sheath and irrigation fluid 52, as is generally described above.

Although the specific embodiments have been described in some detail, by way of illustration and for clarity of understanding, a variety of modifications, adaptations and alternatives will be obvious to those of skill in the art. Therefore, the scope of the present invention is limited solely by the appended claims.

What is claimed is:

1. A method for treating tumorous tissue, the method comprising:

inserting a needle of a probe having an ultrasound transducer into tissue adjacent a tumor;

targeting a blood supply to the tumor based on images provided by said ultrasound transducer; and energizing said needle to destroy said blood supply without targeting the bulk of the tumor by creating coagulation around the tumor.

2. A method for treating tumorous tissue, the method comprising:

inserting a needle of a probe into tissue adjacent a tumor, wherein said probe includes an ultrasound transducer;

sensing a bloodflow leading to the tumorous tissue with the ultrasound transducer of the probe;

further positioning the needle in said tissue based on the location of bloodflow detected by the ultrasound transducer;

coagulating the bloodflow to the tumor tissue by energizing a conductive surface on the needle with electrosurgical power; and verifying stoppage of bloodflow to tumor tissue by sensing with said ultrasound transducer.

3. A method as claimed in claim 2, wherein the inserting step is directed toward the bloodflow with a Doppler ultrasound image provided from the sensing step.

4. A method as claimed in claim 2, further comprising sensing a temperature of the tissue with a sensor of the probe.

5. A method as claimed in claim 2, wherein the inserting step comprises extending the needle from a sheath of the probe, and wherein the ultrasound transducer is mounted on the sheath.

* * * * *